(12) United States Patent
Bates et al.

(10) Patent No.: US 8,343,088 B2
(45) Date of Patent: Jan. 1, 2013

(54) APPARATUS AND METHOD FOR TREATING OCCLUDED INFECTION COLLECTIONS OF THE DIGESTIVE TRACT

(76) Inventors: Douglas Bates, La Jolla, CA (US); Steven F Bierman, Del Mar, CA (US)

( * ) Notice: Subject to any disclaimer, the term of this patent is extended or adjusted under 35 U.S.C. 154(b) by 5 days.

(21) Appl. No.: 12/603,469

(22) Filed: Oct. 21, 2009

(65) Prior Publication Data

US 2010/0100105 A1  Apr. 22, 2010

Related U.S. Application Data

(60) Provisional application No. 61/107,261, filed on Oct. 21, 2008.

(51) Int. Cl.
*A61F 2/04* (2006.01)
*A61M 27/00* (2006.01)

(52) U.S. Cl. ........ 604/9; 623/1.11; 623/23.68; 606/108; 606/191

(58) Field of Classification Search .................. 606/108, 606/151, 153, 157, 191, 200; 623/1.11, 23.64, 623/23.65, 23.7, 1.36, 1.42; 604/8, 9
See application file for complete search history.

(56) References Cited

U.S. PATENT DOCUMENTS

| 7,241,736 | B2 | 7/2007 | Hunter et al. | |
|---|---|---|---|---|
| 7,473,417 | B2* | 1/2009 | Zeltinger et al. | 623/1.34 |
| 2003/0120337 | A1* | 6/2003 | Van Tassel et al. | 623/1.23 |
| 2005/0085900 | A1* | 4/2005 | Case et al. | 623/1.24 |
| 2005/0234294 | A1* | 10/2005 | Saadat et al. | 600/104 |
| 2005/0273060 | A1 | 12/2005 | Levy et al. | |
| 2006/0106332 | A1 | 5/2006 | Knudson et al. | |
| 2006/0235077 | A1* | 10/2006 | Taheri | 604/500 |
| 2007/0123973 | A1* | 5/2007 | Roth et al. | 623/1.15 |

FOREIGN PATENT DOCUMENTS

| JP | 04-073067 | 9/1992 |
|---|---|---|
| RU | 2173958 C1 | 9/2001 |

* cited by examiner

*Primary Examiner* — Victor Nguyen
*Assistant Examiner* — Sarah Webb
(74) *Attorney, Agent, or Firm* — Knobbe, Martens, Olson & Bear, LLP

(57) ABSTRACT

A device and method for treating an occluded infection collection along the digestive tract with a stent delivered to an appendix, diverticulum or other anatomical structure of the digestive tract. A device and method to remove an obstruction from an occluded infection collection along the digestive tract with an obstruction removal device delivered to an appendix, diverticulum or other anatomical structure of the digestive tract.

24 Claims, 10 Drawing Sheets

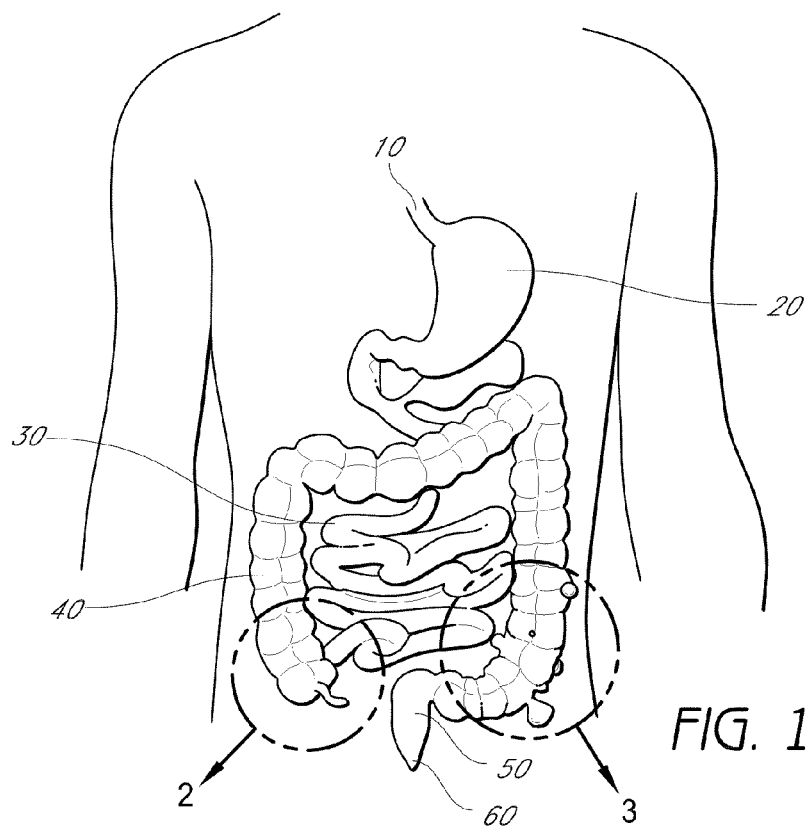
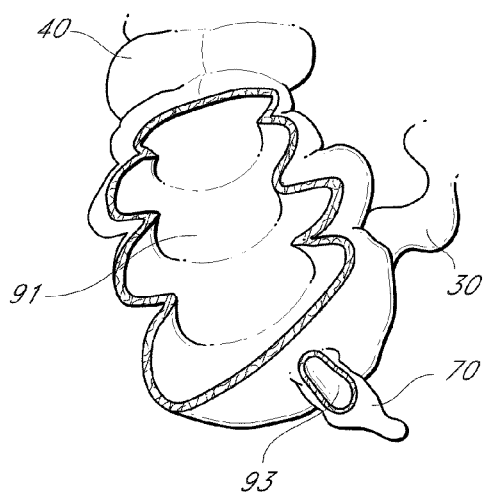
FIG. 2
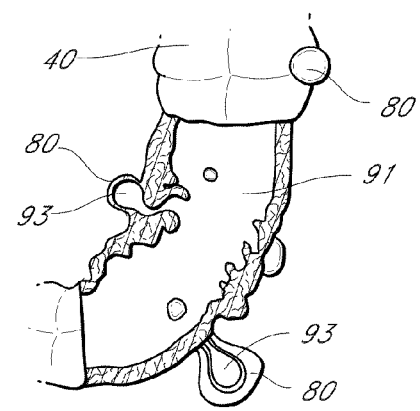
FIG. 3

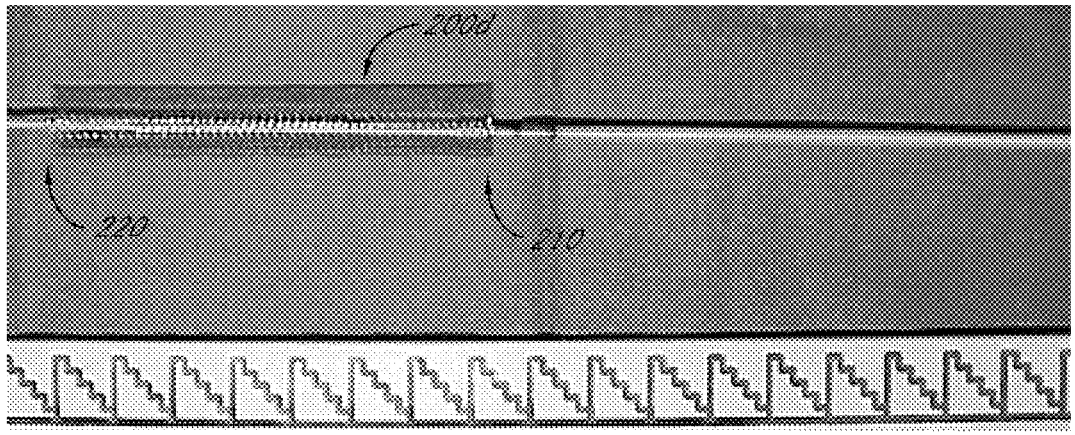
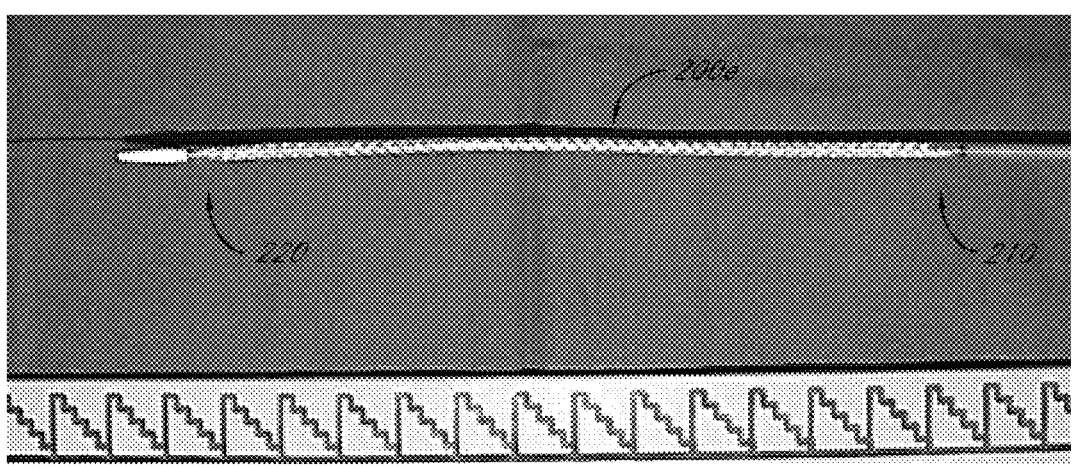
FIG. 15

APPARATUS AND METHOD FOR TREATING OCCLUDED INFECTION COLLECTIONS OF THE DIGESTIVE TRACT

CROSS REFERENCE TO RELATED APPLICATIONS

This application claims the benefit of U.S. Provisional Application No. 61/107,261, filed Oct. 21, 2008, which is hereby incorporated by reference in its entirety.

BACKGROUND

1. Field of the Invention

The invention relates generally to the field of treatment of occluded infection collections, abscesses, inflamed and/or diseased projections in pouch-like portions of the digestive tract, such as an appendix or a diverticular abscess or diverticulum, and more specifically to devices and methods that provide an opening to drain inflamed anatomical structures in the digestive tract without resorting to open surgery or to removal of the anatomical structures.

2. Description of the Related Art

The appendix is a small, tube-like structure attached to the first part of the large intestine, also called the colon. The appendix is typically located in the lower right portion of the abdomen. Removal of the appendix appears to cause no change in digestive function. Appendicitis (or epityphlitis) is an inflammation of the appendix. The cause of appendicitis relates to blockage of the inside of the appendix, known as the lumen. The blockage leads to increased pressure, impaired blood flow, and inflammation. If the blockage is not treated, gangrene and rupture (breaking or tearing) of the appendix can result. Most commonly, feces or calcification blocks the inside of the appendix. Also, bacterial or viral infections in the digestive tract can lead to swelling and inflammation, which squeeze the appendix and cause obstruction to the more distal appendix. This swelling of lymph nodes is known as lymphoid hyperplasia. Traumatic injury to the abdomen may lead to appendicitis in a small number of people. Genetics may be a factor in others. For example, appendicitis that runs in families may result from a genetic variant that predisposes a person to obstruction of the appendiceal lumen.

In the past, appendicitis has lacked an effective medical therapy, so appendicitis is often considered a medical emergency. While some try to treat it with antibiotics, drug-only therapy techniques have had somewhat limited success. Prior treatment of appendicitis required the removal of the appendix by open surgery, laparotomy or laparoscopy. An appendicectomy (or appendectomy) is normally performed as an emergency procedure, when the patient is suffering from acute appendicitis. When treated promptly, most patients recover without difficulty. If treatment is delayed, the appendix can burst, causing infection and even death. Appendicitis is the most common acute surgical emergency of the abdomen.

X rays, ultrasound, and computed tomography (CT) scans can produce images of the abdomen. Plain x rays can show signs of obstruction, perforation (a hole), foreign bodies, and in rare cases, an appendicolith, which is a calcification in the appendix. Ultrasound may show appendiceal inflammation or fluid and can diagnose gall bladder disease and pregnancy. By far the most common test used, however, is the CT scan. This test provides a series of cross-sectional images of the body and can identify many abdominal conditions and facilitate diagnosis when the clinical impression is in doubt. In selected cases, MRI may be used and particularly in women when the cause of the symptoms may be either the appendix or an inflamed ovary or fallopian tube, laparoscopy may be necessary. Laparoscopy avoids radiation, but requires general anesthesia.

The most serious complication of appendicitis is rupture. The appendiceal wall bursts or tears if appendicitis is not diagnosed quickly and goes untreated. Infants, young children, and older adults are at highest risk. A ruptured appendix can lead to peritonitis and abscess. Peritonitis is a dangerous infection that happens when bacteria and other contents of the torn appendix leak into the abdomen. In people with appendicitis, an abscess usually takes the form of a swollen mass filled with fluid and bacteria. In a few patients, complications of appendicitis can lead to organ failure and death.

SUMMARY

In view of the aforementioned shortcomings of traditional treatments and recent purported actions of the appendix, a need exists for apparatus, systems, and methods that can treat appendicitis or other inflammation of structures of the digestive tract less invasively than appendectomies or surgical removal and more effectively than drug treatments alone.

Accordingly, there is provided in accordance with one aspect of the present invention a method for treating an occluded digestive tract projection. The method involves accessing a segment of the digestive track (preferably in a minimally invasive manner) and advancing a catheter to a proximal end of the digestive track projection (e.g., the appendix). A stent is deployed from the catheter into a lumen of the digestive tract projection, preferably at the proximal end of the projection. The stent conducts therethrough body fluids, bacteria and inflammatory components from the digestive tract projection to the digestive track (e.g., to the large intestine). In this manner, the stent can be used to drain an inflamed digestive track projection in a minimally invasive manner.

In some embodiments, the stent, the catheter, or another implant delivered during the same procedure can also be used to deliver a therapeutic agent (e.g., a drug) to the area in or around the digestive track projection. For example, the stent can elute an antibiotic to the tissue forming the digestive track projection to treat infection or other agents to reduce tissue inflammation.

In some embodiments, parts or the whole of the stent can be bioabsorbable and dissolve over a period of time (e.g., over a few weeks or months). In this manner, the stent can maintain patency of the proximal opening into the digestive track projection when infected, but dissolve once the infection has been treated. The shape of the implant can facilitate anchoring the implant in place when the tissue forming the proximal opening into the digestive track projection is inflamed and then releasing when tissue inflammation subsides.

In some embodiments, the stent can be removed through a second procedure. For this purpose, the stent can include structure that facilitates removal of the stent from the proximal opening into the digestive track projection. For example, the stent can include a tab or leash that can be grasped to pull the stent from the proximal opening. Such a tab or leash also can cause the inward collapse or movement of some or all of the stent structure to allow the stent's removal in a less traumatic procedure.

In some embodiments, the stent includes one or more valves operating in one or more lumens to control fluid flow through the stent. For example, the stent can include a one-way valve to allow fluid flow out of the digestive track projection, but inhibit reverse flow.

The implantation procedure in some embodiments also can include the step of removing or macerating obstructions within the digestive track projection. For example, a macerating element can be delivered along with or integrated into the catheter for insertion into a proximal opening of or a space within the digestive track projection. The macerating element can either remove the obstruction from the digestive track projection or macerate. In either event, the obstruction or pieces thereof can be left within the body for natural discharge or can be removed (e.g., by aspiration or basket capture) by the catheter.

BRIEF DESCRIPTION OF THE DRAWINGS

These and other features, embodiments, and advantages of the present invention will now be described in connection with preferred embodiments of the invention, in reference to the accompanying drawings. The illustrated embodiments, however, are merely examples and are not intended to limit the invention.

FIG. 1 illustrates a schematic view of a human digestive tract.

FIG. 2 illustrates a schematic partially exploded sectioned view of a portion of a digestive tract near an appendix.

FIG. 3 illustrates a schematic partially exploded sectioned view of a portion of a digestive tract with diverticulum.

FIG. 15 is a schematic side view of a mesh digestive tract stent with constant lumen width according to one embodiment of the present invention in a compressed configuration and in an expanded configuration.

Figure 4:
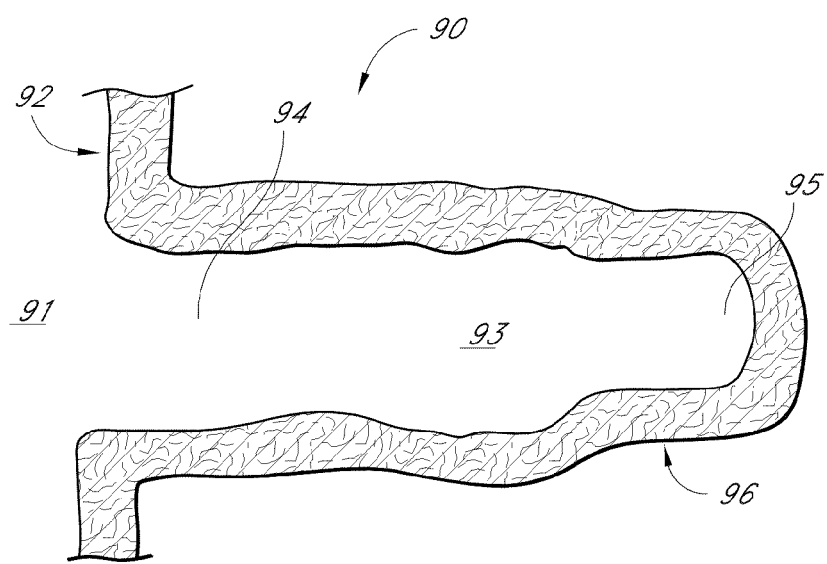
FIG. 4 is a schematic cross-sectional side view of a digestive tract projection, such as an appendix or diverticulum or other similar structures.

Throughout the figures, the same reference numerals and characters, unless otherwise stated, are used to denote like features, elements, components or portions of the illustrated embodiments. In certain instances, similar names may be used to describe similar components with different reference numerals which have certain common or similar features. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF PREFERRED EMBODIMENTS

As should be understood in view of the following detailed description, this application is primarily directed to apparatuses, systems and methods for treating anatomical structures of the digestive tract. Embodiments of the present invention are directed to less-invasive technologies and methods of treating inflamed, infected and/or diseased portions of the digestive tract. The digestive tract can have one or more blind ended projections that are naturally formed or that develop with aging as a response to exposure to bacteria or other environmental factors. Certain projections from the digestive tract, such as the appendix or diverticular abscesses (or diverticulum) can have worm-like or mushroom-like appearances in which recesses or pouches extend into or through the walls of the digestive tract. Various embodiments of the present invention are used to treat projections, or pouch-like extensions, of the digestive tract, such as an appendix or a diverticulum, with a device to reduce inflammation from an infection or other trauma without resorting to open surgery to remove portions of the digestive tract.

FIG. 1 illustrates a schematic representation of a human digestive tract. The digestive tract can be viewed as extending from the mouth, through the throat, down the esophagus 10 into the stomach 20 and to the small intestine 30, proceeding through the large intestine 40 (or colon) to the rectum 50 and terminating at the anus 60. Certain pouch-like structures or projections can extend from or through the walls of the digestive tract, such as at the large intestine 40. For example, some of these projections include the appendix 70 and diverticular abscesses (or diverticulum 80). Additional background information on the appendix 70 and diverticulum 80 can be found in libraries or on the Internet at sites such as Wikipedia or public documents from the National Institutes of Health.

The appendix 70 is a blind ended tube or lumen in fluid connection with the digestive tract. FIG. 2 illustrates a portion of a digestive tract near an appendix 70. Other names for the appendix 70 include the vermiform appendix and cecal appendix. In most people, the appendix 70 develops embryologically and can be found near the junction of the small intestine and the large intestine. The appendix 70 averages 10 cm in length, but can range from 2 to 26 cm. The diameter of the appendix 70 is usually between 7 and 8 mm. The appendix 70 is generally located in the lower right quadrant of the abdomen, or more specifically, the right iliac fossa. Its position within the abdomen corresponds to a point on the surface known as McBurney's point. While the base of the appendix 70 is at a fairly constant location, roughly 2 cm below the ileocaecal valve, the location of the tip of the appendix 70 can vary from being retrocaecal (in roughly three quarters of the population) to being in the pelvis to being extraperitoneal. In rare individuals with situs inversus, the appendix 70 may be located in the lower left side.

The understanding of the function of the appendix 70 is undergoing revisions in the scientific community. A common view was that the appendix 70 was a vestigial, or useless feature with no identified purpose. Doctors, professors and scientists have speculated that the appendix 70 was used in distant ancestors for digesting food, but could not determine how the appendix 70 assisted in the digestive process. More recently, scientists have demonstrated that the appendix 70 may currently serve a purpose for the immune system and/or for maintaining proper beneficial bacteria levels in the digestive tract. For example, studies have shown endocrine cell found in the appendix 70 of 11 week old fetuses that may help biological control and homeostatic mechanism. Some propose that the appendix 70 functions as a lymphatic organ, and studies have shown that the appendix 70 has a relatively high number infection-fighting lymphoid cells, suggesting that it might play a role in the immune system. Some suggest the appendix 70 plays a role in both manufacturing hormones in fetal development as well as functioning to 'train' the immune system, exposing the body to antigens in order that it can produce antibodies. Some doctors have stopped removing the appendix 70 during other surgical procedures as a routine precaution, because it can be successfully transplanted into the urinary tract to rebuild a sphincter muscle and reconstruct a functional bladder. The benefits of keeping the appendix 70 intact in the body are increasing.

Although it was long accepted that the immune tissue, called gut associated lymphoid tissue, surrounding the appendix 70 and elsewhere in the gut carries out a number of important functions, explanations were lacking for the distinctive shape of the appendix 70 and its apparent lack of importance as judged by an absence of side-effects following appendectomy. Some scientists have proposed that the appendix 70 serves as a safe haven for useful bacteria when illness flushes those bacteria from the rest of the intestines. This proposal is based on a new understanding of how the immune system supports the growth of beneficial intestinal bacteria, in combination with many well-known features of the appendix 70, including its architecture and its association with copious amounts of immune tissue. Such a function is expected to be useful in a culture lacking modern sanitation and healthcare practice, where diarrhea may be prevalent. Current epidemiological data show that diarrhea is one of the leading causes of death in developing countries, indicating that a role of the appendix 70 as an aid in recovering beneficial bacteria following diarrhea may be extremely important in the absence of modern health and sanitation practices.

Other anatomical structures in the digestive tract may benefit from a device, system, and/or method of treating the appendix 70. Many people have small pouches in their colons that bulge outward through weak spots, like an inner tube that pokes through weak places in a tire. Each pouch is called a diverticulum 80. Pouches (plural) are called diverticula 80. FIG. 3 shows diverticula 80 in the colon. The condition of having diverticula 80 is called diverticulosis. About 10 percent of Americans over the age of 40 have diverticulosis. The condition becomes more common as people age. About half of all people over the age of 60 have diverticulosis.

When the pouches become infected or inflamed, the condition is called diverticulitis. This happens in 10 to 25 percent of people with diverticulosis. Diverticulosis and diverticulitis are also called diverticular disease. Most people with diverticulosis do not have any discomfort or symptoms. However, symptoms may include mild cramps, bloating, and constipation. The most common sign is tenderness around the left side of the lower abdomen. If infection is the cause, fever, nausea, vomiting, chills, cramping, and constipation may occur as well. The severity of symptoms depends on the extent of the infection and complications. Diverticulitis can lead to bleeding, infections, perforations or tears, or blockages. These complications always require treatment to prevent them from progressing and causing serious illness.

The infection causing diverticulitis can form an abscess in the colon. An abscess is an infected area with pus that may cause swelling and destroy tissue. Sometimes the infected diverticula 80 may develop small holes, called perforations. These perforations allow pus to leak out of the colon into the abdominal area. If the abscess does not clear up with antibiotics, the doctor may need to drain it. To drain the abscess, the doctor uses a needle and a small tube called a catheter. The doctor inserts the needle through the skin and drains the fluid through the catheter. This procedure is called percutaneous catheter drainage. Sometimes surgery is needed to clean the abscess and, if necessary, remove part of the colon. A large abscess can become a serious problem if the infection leaks out and contaminates areas outside the colon. Infection that spreads into the abdominal cavity is called peritonitis. Peritonitis requires immediate surgery to clean the abdominal cavity and remove the damaged part of the colon. Without surgery, peritonitis can be fatal.

A fistula is an abnormal connection of tissue between two organs or between an organ and the skin. When damaged tissues come into contact with each other during infection, they sometimes stick together. If they heal that way, a fistula forms. When diverticulitis-related infection spreads outside the colon, the colon's tissue may stick to nearby tissues. The organs usually involved are the bladder, small intestine, and skin. The most common type of fistula occurs between the bladder and the colon. It affects men more than women. This type of fistula can result in a severe, long-lasting infection of the urinary tract. The problem can be corrected with surgery to remove the fistula and the affected part of the colon.

The scarring caused by infection may cause partial or total blockage of the large intestine. When this happens, the colon is unable to move bowel contents normally. When the obstruction totally blocks the intestine, emergency surgery is necessary. Partial blockage is not an emergency, so the surgery to correct it can be planned.

Treatment for diverticulitis focuses on clearing up the infection and inflammation, resting the colon, and preventing or minimizing complications. An attack of diverticulitis without complications may respond to antibiotics within a few days if treated early enough. An acute attack with severe pain or severe infection may require a hospital stay. Most acute cases of diverticulitis are treated with antibiotics and a liquid diet. If attacks are severe or frequent, the doctor may advise surgery. The surgeon removes the affected part of the colon and joins the remaining sections. This type of surgery, called colon resection, aims to keep attacks from coming back and to prevent complications. The doctor may also recommend surgery for complications of a fistula or intestinal obstruction. If antibiotics do not correct an attack, emergency surgery may be required. Other reasons for emergency surgery include a large abscess, perforation, peritonitis, or continued bleeding.

Emergency surgery usually involves two operations. The first surgery will clear the infected abdominal cavity and remove part of the colon. Because of infection and sometimes obstruction, it is not safe to rejoin the colon during the first operation. Instead, the surgeon creates a temporary hole, or stoma, in the abdomen. The end of the colon is connected to the hole, a procedure called a colostomy, to allow normal eating and bowel movements. The stool goes into a bag attached to the opening in the abdomen. In the second operation, the surgeon rejoins the ends of the colon.

Figure 5:
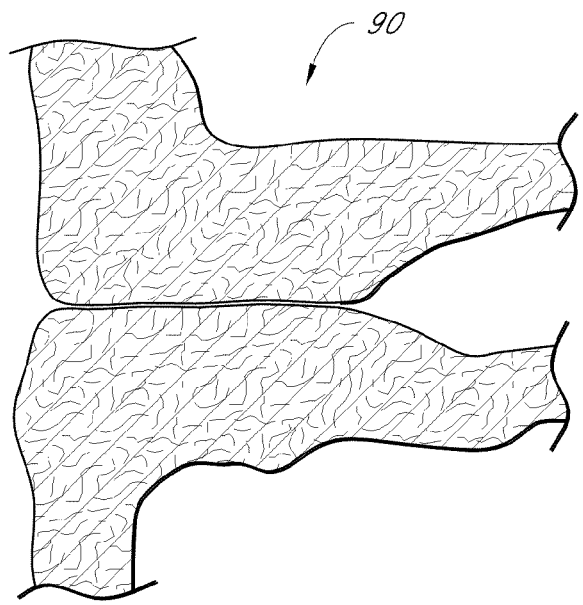
FIG. 5 is a schematic cross-sectional side view of an inflamed, infected, irritated or occluded projection of the digestive tract.

FIG. 4 is a schematic cross-sectional side view of a general digestive tract projection 90, such as an appendix 70 or diverticulum 80 or other similar structures. The digestive tract projection 90 extends from digestive tract lumen 91 from a digestive tract wall 92 with a projection lumen 93 extending from a proximal section 94 to a distal section 95 surrounded by a digestive tract projection wall 96. When the digestive tract projection 90 is healthy, or not inflamed or infected it can perform its function. However, as illustrated in FIG. 5, the digestive tract projection 90 can become inflamed, infected, irritated or occluded, closing a portion of the lumen 93 at the proximal section 94, distal section 95, or both. The digestive tract projection wall 96 can swell and become very sensitive, and potentially perforate or rupture if untreated.

Figure 6:
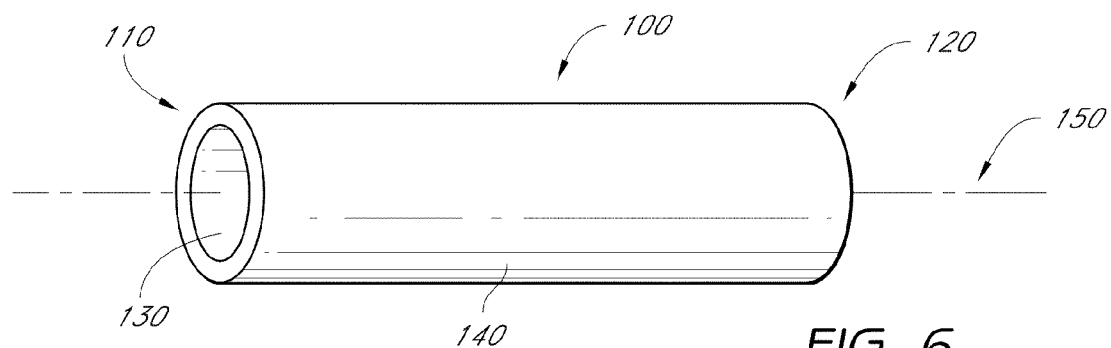
FIG. 6 is a schematic side perspective view of a digestive tract stent according to one embodiment of the present invention.
Figure 7:
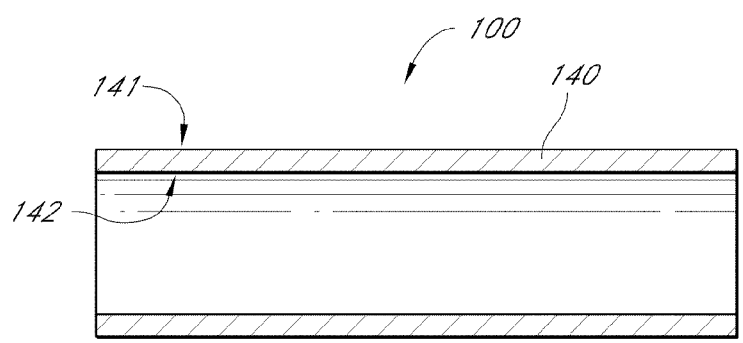
FIG. 7 is a schematic cross sectional side view of a digestive tract stent according to one embodiment of the present invention.

In one embodiment a digestive tract stent 100 has a first, or proximal end 110, a second, or distal end 120, a lumen 130 and a side wall 140. In various embodiments, the stent 100 can have a circular, elliptical, oval, square, rectangular, parallelogram, pentagonal, hexagonal, octagonal or other shape cross-section transverse its longitudinal axis 150. In FIG. 6 the stent 100 has a substantially circular cross-section. FIG. 7 illustrates a sectional view of the stent 100 of FIG. 6 with the side wall 140 having an external surface 141 and an internal surface 142 along the lumen 130. In one embodiment the stent 100 has an extrudable cross-sectional shape with constant width, depth, and/or thickness. In various embodiments the width, height, wall thickness, diameter, circumference, or other geometric characteristics of the stent 100 can be varied. In one embodiment the stent 100 can have an hourglass shape.

In various embodiments treatment of an infection, inflamed, diseased or swollen digestive tract projection 90 with a stent is advantageous over existing surgical removal of the digestive tract projection 90 include, but are not limited to, an easier set up, no requirement for an operating room, wider availability, less cost, procedures can be performed under conscious sedation instead of general anesthesia, procedures are less invasive, reduced risk of complications, reduced risk of bleeding, less expertise required for treatment, a gastrointestinal doctor can perform the procedures, quicker recovery time, less lost time for the patient. Longer term benefits include, but are not limited to, keeping the digestive tract projection 90. Those who have an appendectomy before age 10 are relatively protected from Crohn's disease, while those who have one later are at increased risk of Crohn's. One long term benefit of stent treatment of a digestive tract projection is that surgical complications are reduced or are eliminated. There is a reduced risk of adhesions that may cause small or large bowel obstruction.

In various embodiments the stent 100 is in the range of 0.25 cm-26 cm in length. In one embodiment the stent 100 is roughly 1 cm in length. In one embodiment the stent 100 is roughly 5 cm in length. In one embodiment the stent 100 is roughly 10 cm in length. In various embodiments the stent 100 length is in the range of 3 to 8 cm long. In one embodiment the stent 100 has a width or diameter the same or larger than that of the digestive tract projection lumen 93 width or diameter. Diameter can be measured in French. In one embodiment the stent 100 is delivered by a duodenoscope, which generally currently able to accept stents (in a collapsed or full expansion configuration) with a diameter less than or equal to 12 Fr. In various embodiments the digestive tract projection lumen 93 width or diameter is in the range of 6-9 mm. In one embodiment the stent 100 width or diameter is roughly 7 mm. In one embodiment the stent 100 width or diameter is roughly 8 mm. In one embodiment the stent is formed of a laser cut material. In one embodiment, the stent is formed of interwoven wires.

In one embodiment the stent 100 is made of plastic. In various embodiments the stent 100 can be made of Teflon, polyethylene, polyurethane, polyflex, or other materials. In one embodiment the stent 100 is made of metal. In various embodiments the stent 100 can be made of stainless steel, nickel-titanium alloy, cobalt-tungsten alloy, cobalt-chromium alloy, tantalum alloy, gold, titanium, or other materials. In one embodiment the stent 100 is repositionable during deployment. In one embodiment the stent 100 is repositionable after deployment. In one embodiment the stent 100 is removable after deployment. In one embodiment the stent 100 is repositionable after deployment in a separate procedure. In one embodiment the stent 100 is made of a bioabsorbable material. In one embodiment the stent 100 is made of Vicryl (polyglactin 910). In various embodiments the stent 100 is made of polyester, polyorthoester, polyanhydride, collagen, or other biodegradable material. In one embodiment the stent 100 can be absorbed in a number of days to a number of weeks. In one embodiment the stent 100 dissolves after a period of time. In one embodiment the stent 100 dissolves after a few days. In one embodiment the stent 100 dissolves after a few weeks.

In one embodiment the stent 100 is made of a rigid material, such as a plastic, polymer, or metal. In one embodiment the stent 100 is made of an elastic material, such as certain plastics, polymers, or metals with flexible characteristics. In one embodiment the stent 100 is made of a shape memory material, such as Nitinol. In one embodiment, an elastic or deformable stent 100 can have a first configuration and a second configuration. In one embodiment the first configuration can have a small cross sectional profile to facilitate insertion over a guidewire or in a catheter into a digestive tract projection lumen 93. In one embodiment the second configuration can have a large cross sectional profile to expand the height, width or depth of a digestive tract projection lumen 93. In one embodiment a stent 100 can be expanded or reduced by gas, liquid, and/or fluid pressure. In one embodiment a stent 100 can be expanded or reduced by a balloon. In one embodiment a stent 100 is self expanding.

In one embodiment the stent 100 is at least partially coated with a low-friction substance (e.g., PTFE) to facilitate insertion of the stent 100 into a digestive tract projection lumen 93. In one embodiment the stent 100 is at least partially coated with a low-friction substance on the distal end 120 of the outer wall 141 of the stent 100 to facilitate insertion of the stent 100 into a digestive tract projection lumen 93. In one embodiment the stent 100 is at least partially coated with a high-friction substance to help anchor the stent 100 into a digestive tract projection lumen 93. In one embodiment the stent 100 is at least partially coated with a high-friction substance on the proximal end 110 of the outer wall 141 of the stent 100 to help anchor the stent 100 into a digestive tract projection lumen 93. In one embodiment the stent 100 is at least partially coated with a drug coating to release or elute therapeutic agents, such as an antibiotic, an antimicrobial agent, a growth factors, a growth inhibitors, an antiseptic agent, an anti-inflammatory agent, an antirestinosis agent, or an antioxidant. In one embodiment, the stent 100 is at least partially coated with a hydrophilic polymer coat. In one embodiment the stent 100 is at least partially coated with a silver coat. In one embodiment the stent 100 is at least partially coated with a bacterial delivery coat.

In one embodiment the stent 100 is sterile. In one embodiment the stent 100 comprises media eluting material. In one embodiment the stent 100 comprises pores on the surface or other drug storage systems for drug loading. In one embodiment the media is a drug or therapeutic agent. In one embodiment the media is one or more antibiotics. In one embodiment the media is a growth factor. In one embodiment the media is growth inhibitor. In one embodiment the media is bacteria to provide for beneficial flora to the digestive tract. In one embodiment the media is an antimicrobial agent. In one embodiment the media is delivered over a time-delayed or extended time-release means. In one embodiment an antibiotic is initially released, followed by a time-delayed release of beneficial flora after the antibiotics have dispersed.

In one embodiment, a media or therapeutic agent is delivered to the digestive tract projection through one or more injection ports on a catheter. In one embodiment, the media or therapeutic agent is delivered to the digestive tract projection through one or more injection ports on an expandable balloon. In one embodiment, a media or therapeutic agent is delivered to the digestive tract projection through one ore more injection ports on a stent. In one embodiment, the media or therapeutic agent is delivered simultaneous with the delivery of the stent 100. In one embodiment, the media or therapeutic agent is delivered before or after the delivery of the stent 100. Suitable media or therapeutic agents include, but are not limited to, an antibiotic agent, beneficial flora, an antimicrobial agent, a growth factors, a growth inhibitors, an antiseptic agent, an anti-inflammatory agent, an antirestinosis agent, or an antioxidant.

In one embodiment the stent 100 can have a valve 160 disposed in the lumen 130. In one embodiment the valve 160 is disposed between the proximal end 110 and the distal end 120 of the stent 100. In one embodiment the valve 100 is located at or near the proximal end 110. In one embodiment the valve 100 is located at or near the distal end 120. In one embodiment the valve 100 is a one-way valve that allows fluid or particle flow in one direction and reduces or eliminates flow in the opposite direction. In one embodiment the valve 100 is a one-way valve that promotes drainage of the digestive tract projection lumen 93. In one embodiment the valve 100 is a one-way valve that prevents reflux of digestive tract lumen 91 contents into the digestive tract projection lumen 93.

Figure 8:
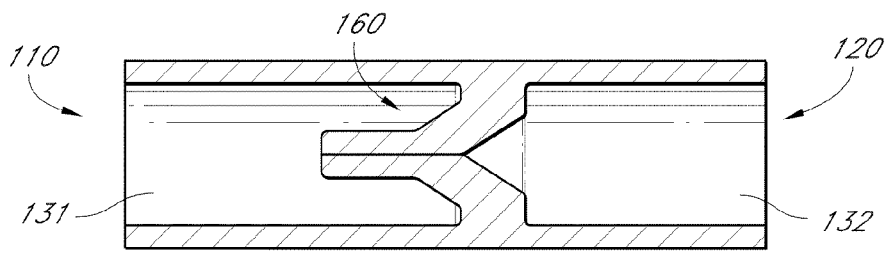
FIG. 8 is a schematic cross sectional side view of a digestive tract stent with a valve in a decreased flow configuration according to one embodiment of the present invention.
Figure 9:
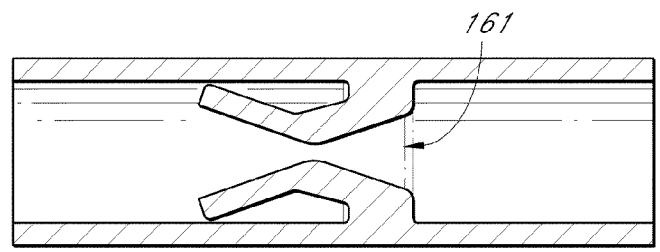
FIG. 9 is a schematic cross sectional side view of the digestive tract stent with a valve of FIG. 8 with the valve in an increased flow configuration.

In one embodiment valve 100 is duck-bill valve. In one embodiment valve 100 has two or more opposed surfaces that can touch each other to occlude or restrict the lumen 130, and that can be actuated by pressure differential between the proximal end 110 and the distal end 120 of the stent 100. In one embodiment deformation of the stent 100 can open or close the valve 160. In one embodiment valve 100 is a flap valve. In one embodiment valve 100 has one or more biased or spring loaded or deflectable surfaces. As shown in FIG. 8 a valve 100 can be configured to restrict or fully occlude flow within the lumen 130 between a proximal lumen section 131 and a distal lumen section 132, and as shown in FIG. 9 the valve 100 can be configured to allow flow from the distal lumen section 132 to the proximal lumen section 131.

Figure 10:
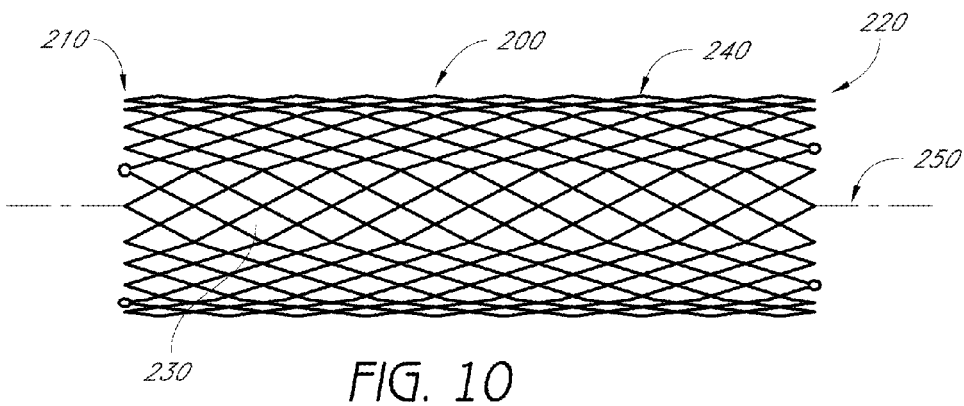
FIG. 10 is a schematic side view of a mesh digestive tract stent according to one embodiment of the present invention.
Figure 11:
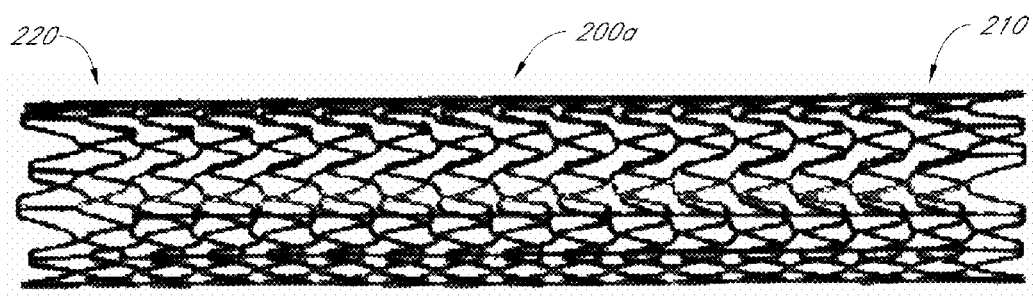
FIG. 11 is a schematic side view of a mesh digestive tract stent according to one embodiment of the present invention with constant lumen width.
Figure 12:
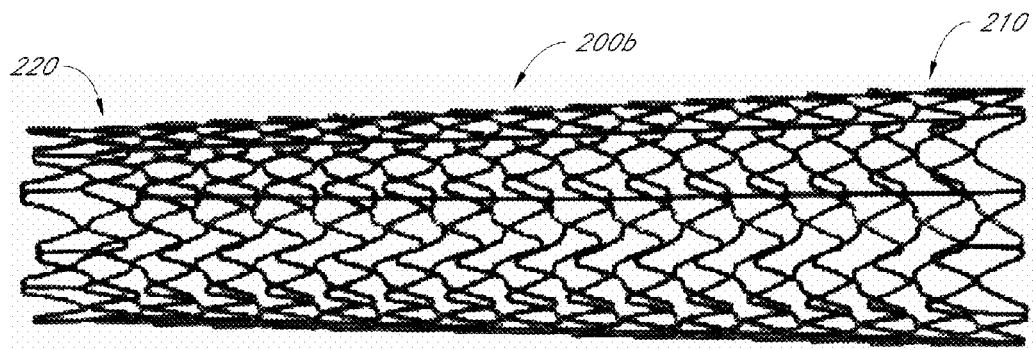
FIG. 12 is a schematic side view of a mesh digestive tract stent according to one embodiment of the present invention with linearly varying lumen width.
Figure 13:
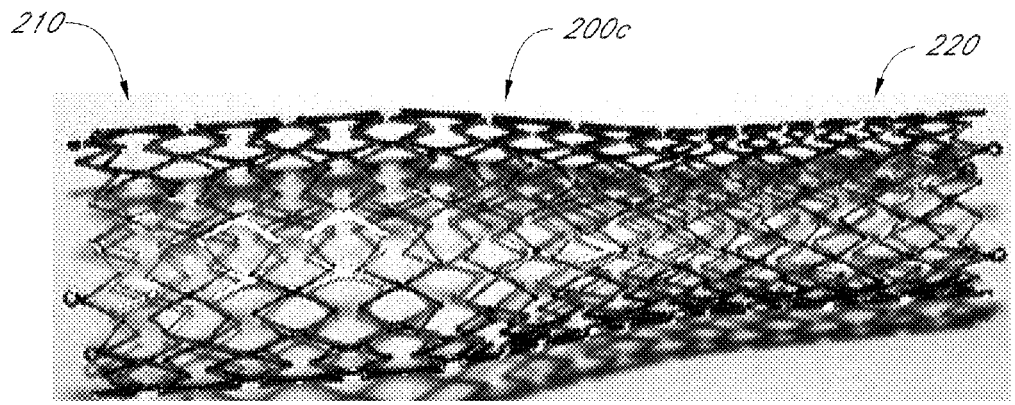
FIG. 13 is a schematic side view of a mesh digestive tract stent according to one embodiment of the present invention with varying lumen width.
Figure 14:
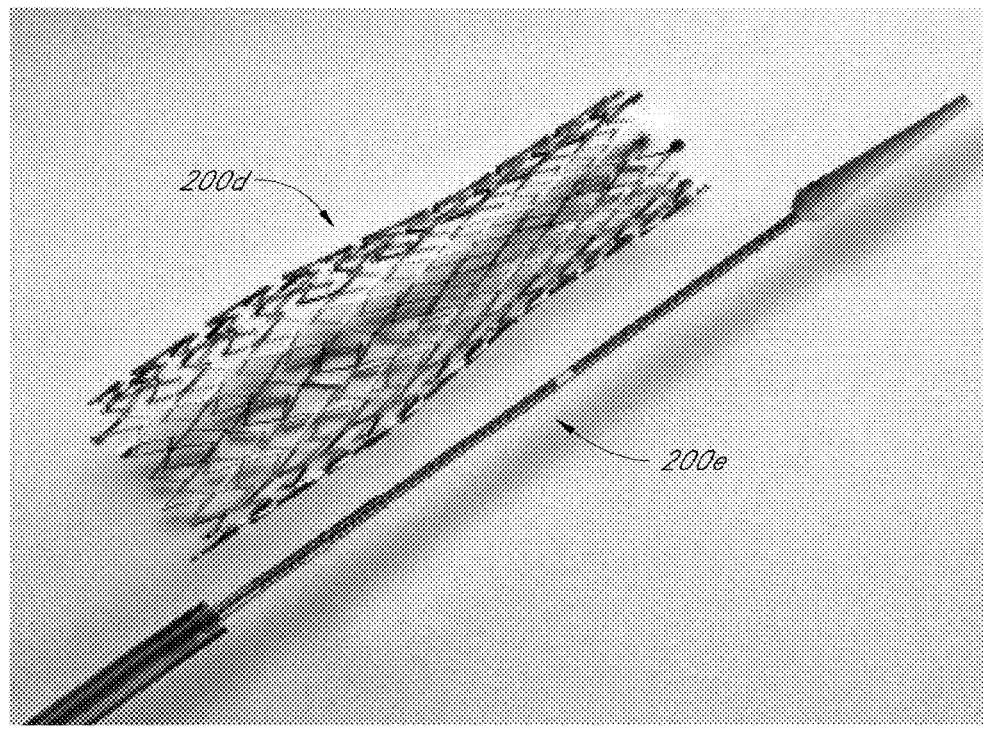
FIG. 14 is a schematic side view of a mesh digestive tract stent with varying lumen width according to one embodiment of the present invention in a compressed configuration and in an expanded configuration.

In one embodiment a mesh digestive tract stent 200 includes an expandable mesh structure. In one embodiment a mesh stent 200 is capable of being delivered in a small profile and expanding into a large profile to facilitate flow in at least one direction in a digestive tract projection lumen 93. In one embodiment a mesh stent 200 is self expanding. In one embodiment a mesh stent 200 expanded or reduced by gas, liquid, and/or fluid pressure. In one embodiment a mesh stent 200 can be expanded or reduced by a balloon (e.g. by an expandable balloon placed inside the stent). In one embodiment a mesh stent 200 has a nonabrasive or atraumatic distal and/or proximal end. Mesh stent 200 can have many of the characteristics described in relation to stent 100. In any of the stent embodiments described herein, features of a stent in one embodiment can be combined with features of a stent in another embodiment. In one embodiment a mesh digestive tract stent 200 has a first, or proximal end 210, a second, or distal end 220, a lumen 230 and a mesh wall 240. In various embodiments, the mesh stent 200 can have a circular, elliptical, oval, square, rectangular, parallelogram, pentagonal, hexagonal, octagonal or other shape cross-section transverse its longitudinal axis 250. In FIG. 10 the mesh stent 200 has a substantially circular cross-section. In one embodiment a mesh stent 200a can have a constant lumen width, as shown in FIG. 11. In some embodiment a width reflects a diameter. In various embodiments, either the proximal end 210 width or the distal end 220 width can be larger than the other. In various embodiments, a width of the stent 200 between the proximal end 210 and the distal end 220 can be larger or smaller than either or both of the proximal end 210 width or the distal end 220 width. In one embodiment a mesh stent 200b can have a linearly varying lumen width, as shown in FIG. 12. In one embodiment a mesh stent 200c can have a varying lumen width, as shown in FIG. 13. In one embodiment a mesh stent 200 can have an expanded configuration 200d and a compressed configuration 200e, as shown in FIGS. 14 and 15.

Figure 16:
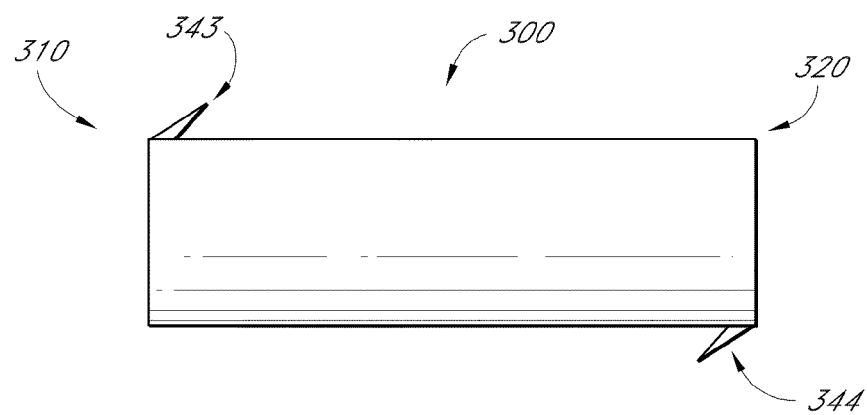
FIG. 16 is a schematic side view of a digestive tract stent with one or more anchors according to one embodiment of the present invention.

FIG. 16 illustrates one embodiment a digestive tract stent 300 with a proximal end 310 and a distal end 320 has one or more anchors. In one embodiment, the stent 300 has one or more proximal anchors 343. In one embodiment, the stent 300 has one or more distal anchors 344. In one embodiment the anchors are use to prevent migration in one or more directions. Any of the anchors can be a rough surface, coating, barb, or surface feature that helps retain the stent 300 in the digestive tract projection lumen 93. Any of the anchors can be disposed at an end or anywhere along the length of the stent 300. The angle of a barb or orientation of an anchor can be in any direction.

Figure 17:
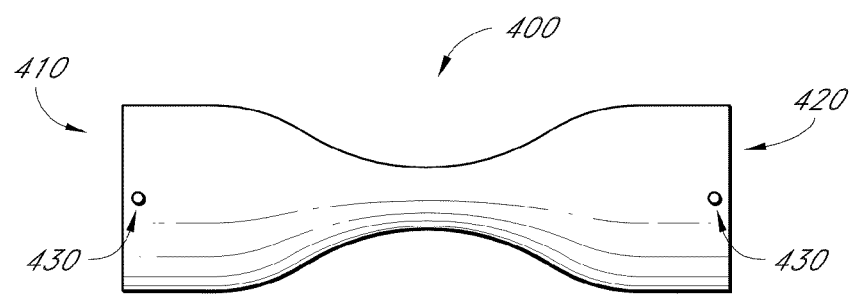
FIG. 17 is a schematic side view of an hourglass shaped digestive tract stent according to one embodiment of the present invention.

In one embodiment a digestive tract stent 400 with a proximal end 410 and a distal end 420 has an hourglass configuration, as illustrated in FIG. 17. In one embodiment the hourglass configuration can be configured to help retain the stent 400 in a position in the digestive tract projection lumen 93 by holding a portion of the tissue of the digestive tract projection lumen 93 between the proximal end 410 and a distal end 420. In one embodiment the hourglass configuration can have one or more anchors to help retain the stent 400 in a position in the digestive tract projection lumen 93. In any embodiment a stent can have a marker 430. In one embodiment the marker 430 is radiopaque to facilitate visualization under fluoroscopy or other scanning or visualization techniques. In various embodiments the marker 430 is a dot, a ring, a shape for visualization and/or identification of the stent and/or stent orientation. In various embodiments, the visualization is facilitated by using stent wire with radiopaque cores or radioopaque coatings or platings.

Figure 18:
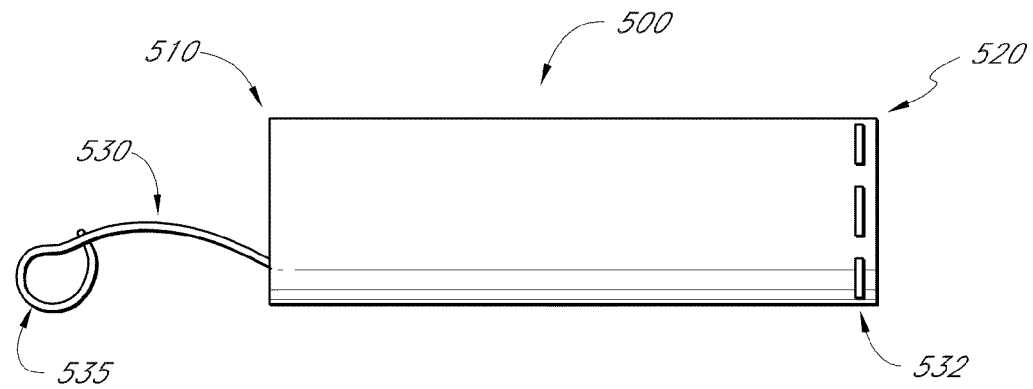
FIG. 18 is a schematic side view of a digestive tract stent with a tether according to one embodiment of the present invention.
Figures 19, 20:
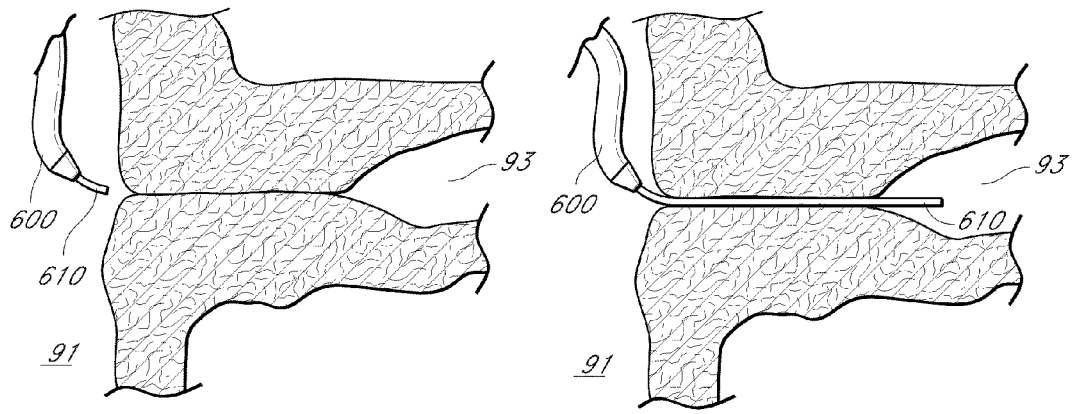
FIGS. 19-22 are schematic side view partial cross sectional views of the delivery of a stent to a digestive tract projection lumen using a catheter and a guide wire according to one embodiment of the present invention.
Figures 21, 22:
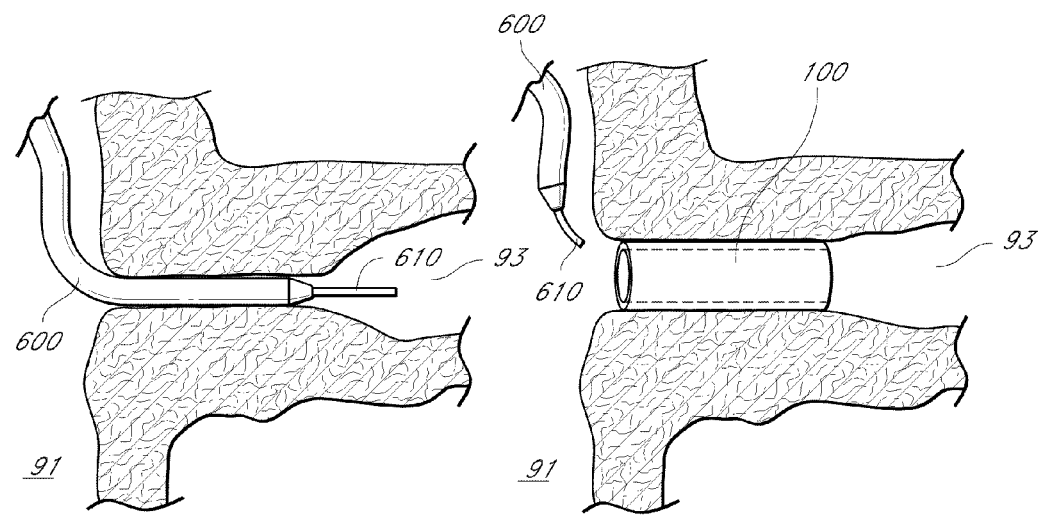

In one embodiment a digestive tract stent 500 with a proximal end 510 and a distal end 520 has a tether 530, as illustrated in FIG. 18. In various embodiments the tether can be attached to any portion of the stent 500 to facilitate repositioning or removal of the stent 500. In one embodiment the tether 530 has a snare feature 535, such as a loop, that can be used to grab the tether 530. In one embodiment the tether 530 is connected to the distal end 520 at a tether interface 532. The tether 530 can be moved in a proximal direction to collapse or reduce the cross sectional size or profile of the distal end 502 of the stent 500 in order to facilitate insertion, repositioning, and/or removal of the stent 500. In one embodiment, the stent 500 can be delivered with the tether 530 being pulled or moved proximally so the distal end 520 is small to facilitate insertion into a lumen. In one embodiment the tether 530 can be pulled or moved proximally to reduce the size of the distal end 520 to facilitate removal of the stent 500 from a lumen. In one embodiment the tether 530 can be pulled or moved proximally to reduce the size of the distal end 520 to disengage a distal anchor (such as distal anchor 344) to facilitate removal of the stent 500 from a lumen. The tether interface 532 can be located anywhere on the stent 500.

In one embodiment of a digestive tract stent and method for delivery and/or removal of a stent, a spiral shaped device and methods associated with the deployment of a device for deployment which can be configured in a first delivery configuration to and/or from a second deployed spiral configuration is described in U.S. Pat. No. 5,536,274 issued Jul. 16, 1996 to Neuss can be used. U.S. Pat. No. 5,536,274 is incorporated by references as a whole, including FIGS. 1-6 and FIGS. 11a-11e, col. 2, l. 13 to col. 3, line 30, col. 3 line 31-col. 4 line 49, col. 4, ll. 63-65, col. 7, line 59 to col. 8, line 28 and col. 8, line 41 to col. 9, line 47.

FIGS. 19-22 illustrate various potential steps in one embodiment of the delivery of a stent 100 to a digestive tract projection lumen 93 using a catheter 600 and a guide wire 610 according to one embodiment of the present invention. In various embodiments a catheter 600 with a stent 100 can be directed to the digestive tract lumen 91 near a digestive tract projection lumen 93 opening from an endoscope, from an oral endoscopic path, from an anal endoscopic path, from the mouth, from the anus, from laparoscopic insertion, from piercing the digestive tract superior to or inferior to the digestive tract projection lumen 93 opening and inserting the catheter 600. In one embodiment the laparoscopic insertion is made in the stomach. In one embodiment the laparoscopic insertion is made in the small intestine. In one embodiment the laparoscopic insertion is made in the large intestine superior or inferior to the digestive tract projection lumen. In one embodiment access to the digestive tract projection lumen 93 is provided by piercing the projection wall 96. In one embodiment, piercing the projection wall 96 is accomplished with a cannulated needle and/or a guidewire. In one embodiment the catheter 600 has a guide wire 610 which can be inserted into the digestive tract projection lumen 93 to create a path for the stent 100 to be delivered. In one embodiment aspects of a procedure can be conducted under endoscopy. In one embodiment the procedure is conducted using a radiograpically direct procedure, for example, under fluoroscopy. Fluoroscopy and other radiographically direct procedures each have an added benefit of being able to visualize bleeding or perforations. This approach would eliminate the need to use a large amount of injected air or gas via an endoscopic tube, and would reduce the risk of pushing fecal material through a weakness in the bowel wall or into the appendix. In one embodiment aspects of a procedure can be conducted under computed tomography (CT) guidance. In one embodiment aspects of a procedure can be conducted under ultrasound imagery. In one embodiment aspects of a procedure can be conducted under MRI. In one embodiment aspects of a procedure can be conducted in a catheter lab. In all such embodiments where access is gained through a naturally occurring orifice within the body, the treatment method eliminates the need for an operating room to treat the occluded digestive tract projection (e.g., an appendicitis). Such procedures only require a procedure room, but do not need a sterile environment. On the other hand, prior courses to treat an appendicitis involved invasive surgery, which required an operating room with the accompanying sterile environment, procedure and expense.

In a further embodiment, the placement of the stent 100 can occur after an incision has been made partially through a wall of the connection portion between the digestive track lumen 91 and the appendix 70 (or the diverticulum 80) in a manner similar to a papillotomy. Such an incision will increase the sized of the lumen 93, once stented open, between the digestive track lumen 91 and the appendix 70 (or the diverticulum 80). A larger lumen size can enhance the release of matter from the appendix 70 and reduce the likelihood of later inflammation of the appendix 70 (or the diverticulum 80).

Figure 23:
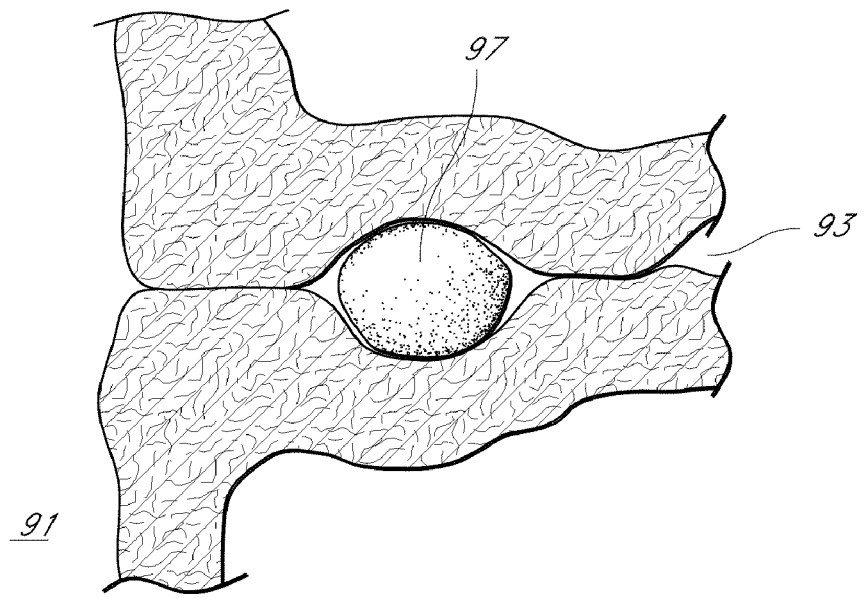
FIG. 23 is a schematic partially cross-sectional side view of an obstruction in a digestive tract projection lumen.
Figure 24:
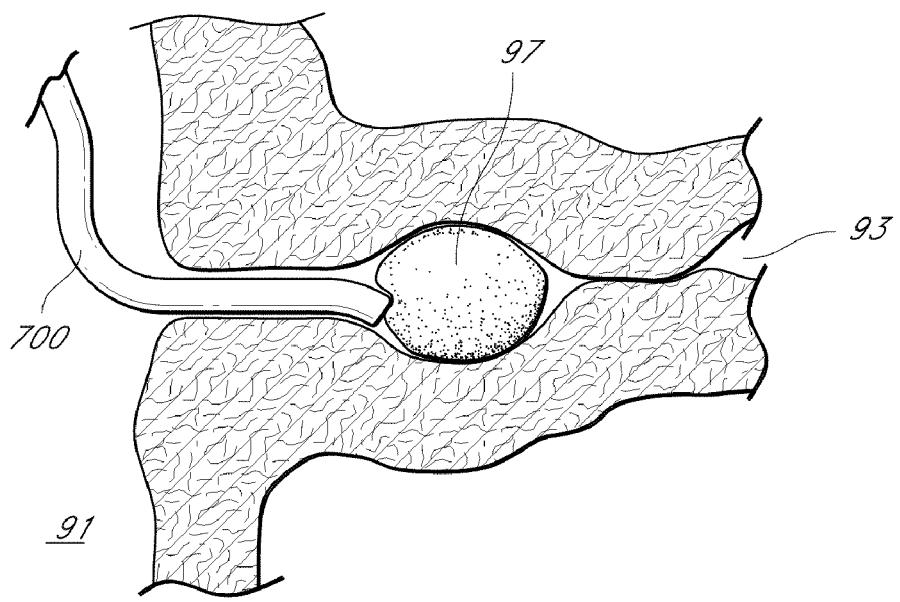
FIG. 24 is a schematic partially cross-sectional side view of an obstruction removal device according to one embodiment of the present invention.
Figure 25:
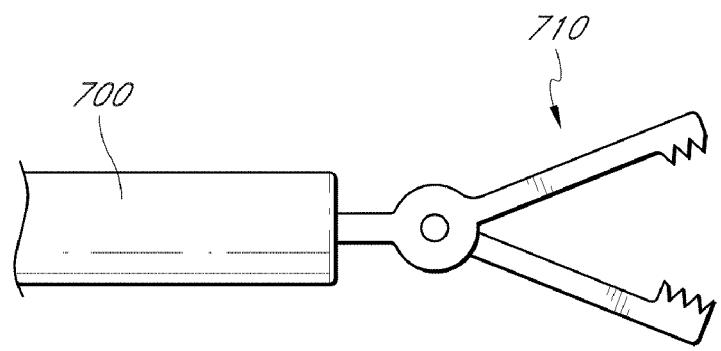
FIG. 25 is a schematic side view of an obstruction removal device with two fingers for manipulating, grabbing, macerating, crushing, and/or compressing the obstruction according to one embodiment of the present invention.
Figure 26:
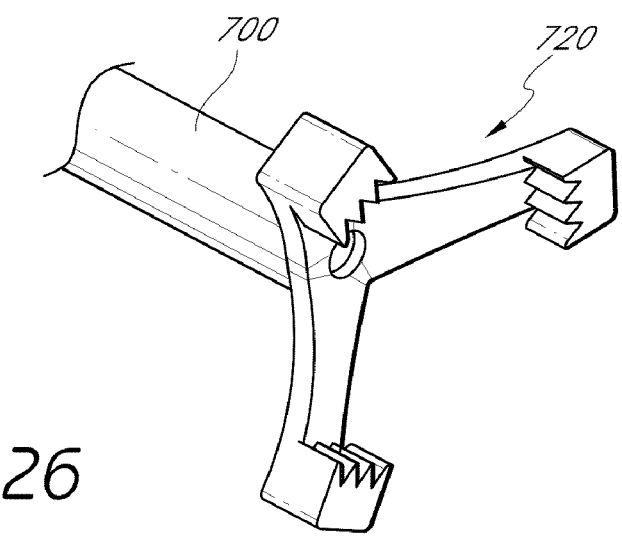
FIG. 26 is a schematic perspective view of an obstruction removal device with a plurality of linked fingers for manipulating, grabbing, macerating, crushing, and/or compressing the obstruction according to one embodiment of the present invention.
Figure 27:
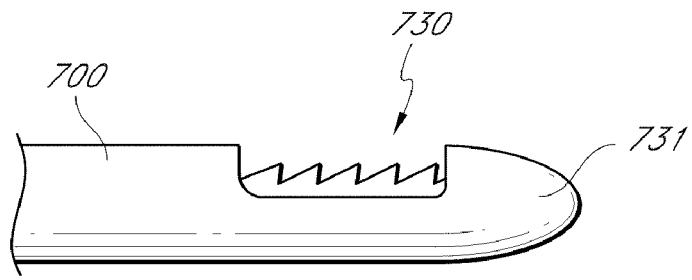
FIG. 27 is a schematic side view of an obstruction removal device with a cutter according to one embodiment of the present invention.

FIG. 23 illustrates an obstruction 97, which can be a stone, calcification, abscess, pus, or other material which can reside in or block the digestive tract projection lumen 93. In one embodiment an obstruction removal device 700 can be directed to the digestive tract projection lumen 93 to remove or reduce the size of the obstruction 97. In various embodiments a obstruction removal device 700 can be directed to the digestive tract lumen 91 near a digestive tract projection lumen 93 opening from an endoscope, from an oral endoscopic path, from an anal endoscopic path, from the mouth, from the anus, from laparoscopic insertion, from piercing the digestive tract superior to or inferior to the digestive tract projection lumen 93 opening and inserting the obstruction removal device 700. In one embodiment the obstruction removal device 700 has a guide wire (not illustrated here) which can be inserted into the digestive tract projection lumen 93 to create a path for the obstruction removal device 700 to get near the obstruction 97, as shown in FIG. 24. In one embodiment the obstruction removal device 700 is a suction device which can aspirate the obstruction 97 from the digestive tract projection lumen 93 with pressure differential. In one embodiment the obstruction removal device 700 has a sharp point or edge for piercing or cutting the obstruction 97. In one embodiment the obstruction removal device 700 has a gripping mechanism for grabbing the obstruction 97. In one embodiment the obstruction removal device 700 has two or more fingers 710 for manipulating, grabbing, macerating, crushing, and/or compressing the obstruction 97. See FIG. 25. In various embodiments the obstruction removal device 700 can have two, three, four or more fingers 710. In one embodiment the obstruction removal device 700 has a hinged linkage with two, three, or more links 720 for manipulating, grabbing, macerating, crushing, and/or compressing the obstruction 97. See FIG. 26. In one embodiment the obstruction removal device 700 includes one or more nets. In one embodiment the obstruction removal device 700 includes one or more snares or baskets. Suitable baskets are disclosed in U.S. Pat. No. 5,330,482, which is hereby incorporated by reference. In one embodiment the obstruction removal device 700 includes one or fibers for ensnaring the obstruction 97. In one embodiment the obstruction removal device 700 includes a medium or media for dissolving the obstruction 97. In one embodiment the obstruction removal device 700 includes a cutter 730. See FIG. 27. In one embodiment the cutter 730 is a linear cutter. In one embodiment the cutter 730 is a rotational cutter. In one embodiment the cutter 730 is a reciprocating cutter. In one embodiment the cutter 730 comprises one or more blades. In one embodiment the cutter 730 comprises one or more gear teeth. In one embodiment the obstruction removal device 700 includes an atraumatic distal tip to facilitate insertion into a swollen lumen. Any of the obstruction removal device 700 embodiments can be combined.

It will be understood that the foregoing is only illustrative of the principles of the invention, and that various modifications, alterations, and combinations can be made by those skilled in the art without departing from the scope and spirit of the invention. Accordingly, it is not intended that the invention be limited, except as by the appended claims.

What is claimed is:

1. A method of treating an occluded digestive tract projection, comprising:
    providing a stent comprising a proximal portion, a distal portion, and a stent lumen extending between the proximal portion and the distal portion, the stent configured to allow a fluid flow in a first direction through the stent lumen and to inhibit fluid flow in a second direction through the stent lumen;
    advancing a catheter through at least a portion of a digestive tract to a proximal end of a digestive tract projection;
    deploying the stent from the catheter to a lumen of the digestive tract projection; and
    positioning the distal portion of the stent in the lumen of the digestive tract projection and the proximal portion of the stent proximate the proximal end of the digestive tract projection to allow fluid flow in the first direction from the distal portion to the proximal portion out of the digestive track projection, and to inhibit fluid flow in the second direction from the proximal portion to the distal portion into the digestive track projection.

2. The method of claim 1 wherein the digestive tract projection is an appendix.

3. The method of claim 1 wherein the digestive tract projection is a diverticulum.

4. The method of claim 1 further comprising the delivery of a therapeutic agent.

5. The method of claim 1 wherein the catheter is advanced using an endoscope.

6. The method of claim 1 wherein the catheter is advanced through a laparoscopic insertion.

7. The method of claim 1 wherein the stent further comprises one or more one-way valves to control fluid flow through the stent.

8. The method of claim 1 wherein the stent further comprises one or more regions with varying width.

9. The method of claim 1 further comprising delivering beneficial flora to the digestive tract projection.

10. The method of claim 1 wherein the stent further comprises one or more coating selected from the group consisting of a biocompatible coating, a low-friction coating, a high-friction coating, a hydrophilic polymer coating, a silver coating, and a therapeutic agent coating.

11. The method of claim 1 further comprising securing a securing feature on the stent to the digestive tract projection.

12. The method of claim 1 further comprising tethering a tether on the stent to the digestive tract projection.

13. A method of treating an occluded digestive tract projection, comprising:
    providing a stent comprising a stent lumen and a one-way valve configured to open to allow a fluid flow in a first direction through the stent lumen and to close to inhibit fluid flow in a second direction through the stent lumen;
    advancing a catheter to a proximal end of a digestive tract projection; and
    deploying the stent from the catheter to a lumen of the digestive tract projection with the one-way valve oriented to open to allow fluid flow out of the lumen to the proximal end of the digestive track projection, and to close to inhibit fluid flow into the lumen from the proximal end of the digestive track projection.

14. The method of claim 13 wherein the digestive tract projection is an appendix.

15. The method of claim 13 wherein the digestive tract projection is a diverticulum.

16. The method of claim 13 further comprising the delivery of a therapeutic agent.

17. The method of claim 13 wherein the catheter is advanced using an endoscope.

18. The method of claim 13 wherein the catheter is advanced through a laparoscopic insertion.

19. The method of claim 13 wherein the stent further comprises two or more valves to control fluid flow through the stent.

20. The method of claim 13 wherein the stent further comprises one or more regions with varying width.

21. The method of claim 13 further comprising delivering beneficial flora to the digestive tract projection.

22. The method of claim 13 wherein the stent further comprises one or more coating selected from the group consisting of a biocompatible coating, a low-friction coating, a high-friction coating, a hydrophilic polymer coating, a silver coating, and a therapeutic agent coating.

23. The method of claim 13 further comprising securing a securing feature on the stent to the digestive tract projection.

24. The method of claim 13 further comprising tethering a tether on the stent to the digestive tract projection.

* * * * *